United States Patent
Ramirez (10) Patent No.: US 11,846,616 B2
(45) Date of Patent: Dec. 19, 2023

(54) AUTOMATIC CALIBRATION OF LABORATORY INSTRUMENTS

(71) Applicant: Beckman Coulter, Inc., Brea, CA (US)

(72) Inventor: Carlos A. Ramirez, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 1127 days.

(21) Appl. No.: 16/534,066

(22) Filed: Aug. 7, 2019

(65) Prior Publication Data

US 2020/0049675 A1    Feb. 13, 2020

Related U.S. Application Data (60) Provisional application No. 62/715,652, filed on Aug. 7, 2018.

(51) Int. Cl.
| | |
|---|---|
| *G01N 33/00* | (2006.01) |
| *G16H 10/40* | (2018.01) |
| *G16H 10/60* | (2018.01) |
| *G01D 18/00* | (2006.01) |
| *G01N 31/00* | (2006.01) |

(52) U.S. Cl.
CPC ........... *G01N 33/00* (2013.01); *G01D 18/002* (2013.01); *G01N 31/00* (2013.01); *G16H 10/40* (2018.01); *G16H 10/60* (2018.01)

(58) Field of Classification Search
CPC ........ G01N 33/00; G01N 31/00; G16H 10/40; G16H 10/60; G01D 18/002
See application file for complete search history.

(56) References Cited

U.S. PATENT DOCUMENTS

| | | | | |
|---|---|---|---|---|
| 5,692,220 | A * | 11/1997 | Diamond | G01N 35/0092 706/924 |
| 6,438,533 | B1 * | 8/2002 | Spackman | G06Q 10/10 706/45 |

(Continued)

FOREIGN PATENT DOCUMENTS

JP    S57161635    10/1982

OTHER PUBLICATIONS

Structured Query Language (SQL), stable version 2016.*

(Continued)

*Primary Examiner* — Mohamed Charioui
*Assistant Examiner* — Lynda Dinh
(74) *Attorney, Agent, or Firm* — Schwegman Lundberg & Woessner, P.A.

(57) ABSTRACT

Improved systems and methods for laboratory instrument calibration. A laboratory instrument retrieves a number of sets of past quality control parameters from a data structure. Each set includes a recovered value and a timestamp. The recovered value is equal to an output value adjusted by an initial calibration factor. The laboratory instrument determines that the number of sets is greater than a threshold and that each of the past quality control parameters has a timestamp that is within a time threshold. The laboratory instrument computes an updated calibration factor such that when the updated calibration factor is applied to a representative value of the recovered values, the representative value equals the expected recovered value. The instrument updates the data structure with the calibration factor such that the calibration factor is used in subsequent testing of patient specimens.

20 Claims, 7 Drawing Sheets

(56) References Cited

U.S. PATENT DOCUMENTS

| | | | | |
|---|---|---|---|---|
| 6,556,951 | B1* | 4/2003 | Deleo | G16H 10/20 |
| | | | | 702/182 |
| 6,787,361 | B1* | 9/2004 | Klee | G01N 33/50 |
| | | | | 702/22 |
| 7,711,503 | B2* | 5/2010 | Yundt-Pacheco | G01D 18/00 |
| | | | | 700/109 |
| 2016/0356800 | A1* | 12/2016 | Glavina | G16Z 99/00 |

OTHER PUBLICATIONS

"International Application Serial No. PCT/US2019/045432, International Search Report dated Oct. 25, 2019", 4 pgs.
"International Application Serial No. PCT/US2019/045432, Written Opinion dated Oct. 25, 2019", 5 pgs.

* cited by examiner

# AUTOMATIC CALIBRATION OF LABORATORY INSTRUMENTS

CLAIM FOR PRIORITY

This patent application claims the benefit of priority to U.S. Provisional Application Ser. No. 62/715,652, filed Aug. 7, 2018, which is incorporated by reference herein in its entirety.

BACKGROUND

Laboratory instruments can perform automated analysis of patient specimens such as blood or urine. In order to ensure accurate results, laboratory instruments undergo periodic calibration to compensate for factors such as environmental conditions and equipment age. If a laboratory instrument includes multiple modules, then each module may be separately calibrated.

Existing solutions for calibrating instruments fail to take advantage of historical calibration data, resulting in imperfect instrument calibration. Moreover, existing solutions are time consuming, require subject matter expertise, and can cause laboratory downtime while troubleshooting and recalibration takes place. A delay in testing of patient specimens causes results to be delayed to patients, physicians, and emergency rooms.

Hence, new solutions are needed for calibration of laboratory instruments.

BRIEF SUMMARY

Improved systems and methods for laboratory instrument calibration are disclosed. In an aspect, a laboratory instrument includes a testing apparatus and a processor. The processor is configured to retrieve, from a data structure, sets of past quality control parameters. Each set includes a timestamp and either an output value or a past calibration factor and a recovered value equal to an output value adjusted by the past calibration factor. The processor is configured to determine that a number of the sets is greater than a threshold and that the timestamp of each set is within a time threshold. The processor is configured to calculate a calibration factor. The processor is configured to calculate a representative value of either the output values or the recovered values, access an expected value, and calculate the calibration factor such that an application of the calibration factor to the representative value equals the expected value. The processor is configured to update the data structure with the calibration factor.

In another aspect, calculating the representative value involves calculating one of a mean, a mode or a median of the output value from each set of past quality control parameters.

In another aspect, calculating the representative value involves de-calibrating each recovered value by removing the respective past calibration factor, and calculating one of a mean, a mode, or a median of the de-calibrated values.

In another aspect, the updating causes the calibration factor to be used in future quality control tests.

In another aspect, responsive to determining that the calibration factor is outside a predefined tolerance, the processor is configured to cease performing calibration and sends an alert.

In another aspect, the instrument is configured to test a patient specimen on a laboratory instrument. The processor is configured to obtain a measurement of a parameter, calculate a recovered value by applying the calibration factor to the measurement, and transmit the recovered value to a display device or in an electronic communication.

In another aspect, the instrument accesses a timestamp indicating a current time, tests a quality control specimen on a laboratory instrument to obtain a measurement of a parameter, calculating a recovered value by applying the calibration factor to the measurement, and storing the recovered value and the timestamp in the data structure.

In another aspect, the processor, responsive to determining that the recovered value is outside a threshold, is configured to cease processing of further specimens and initiating a calibration of the laboratory instrument.

In another aspect, the processor, responsive to determining a diagnostic run, is configured to clear data in the data structure.

The aspects described herein can be implemented on laboratory instruments, using methods, or by a processor executing computer program instructions that are stored on non-transitory computer-readable media.

A better understanding of the nature and advantages of embodiments of the present invention may be factored with reference to the following detailed description and the accompanying drawings.

DETAILED DESCRIPTION

Aspects described herein relate to calibration of laboratory instruments. Non-limiting examples of laboratory instruments include hematology testing instruments, flow cytometry instruments, and particle counters. More particularly, aspects described herein facilitate automatic calibration of laboratory instruments based on historical quality control data. Instrument calibration ensures that measurements obtained on laboratory instruments are adjusted to compensate for different factors such as humidity, temperature, instrument module drift (e.g., of a laser or a flow cell), instrument age, or any combination thereof. These factors are exemplary only, and it should be understood that the systems described may be configured to calibrate instruments based on other parameters.

Calibration relies on data obtained from one or more quality control tests. Quality control tests involve obtain a measurement of a property of a quality control specimen and compare the result with an expected measurement. In a more specific example, a hematology instrument may perform quality control test using a vial of beads or particles. The particles can be manufactured using different processes with different materials. For example, the particles can be plastic, or polystyrene with <2% Divinyl Benzene (DVB). The number, size, and properties of the beads is known and is input into the instrument. Beads can be used to calibrate properties such as conductance, reflectance, fluorescence, radio frequency reflection, or particle size. Testing can be performed periodically (for example, at the start of every day) or on demand.

The quality control measurement is optionally adjusted by a calibration factor, resulting in a recovered value. The calibration factor can be a linear gain or offset, or a set of factors such as a gain and offset, quadratic factors, logarithmic factors, or any combination thereof.

A recovered value is a calibrated output of a measurement. For example, when the calibrated instrument is used to measure a parameter from a patient sample, the recovered value is a value based on a set of values obtained in a laboratory. More specifically, a laboratory instrument obtains a set of recovered values from a patient sample. Statistics are derived from the set of recovered values and presented in a laboratory report to a patient or physician. A recovered value can be de-calibrated, or adjusted, such that an effect of calibration is removed.

For an instrument with multiple modules, calibration can be performed separately for each module. For example, a hematology device that measures human cell parameters may calibrate several different modules such as a red blood cell module, a white blood cell module, or a platelet module. Further, an instrument may separately calibrate modules for volume, radio frequency, and light scatter. Different modules may perform tests in series on a given specimen. Each module may have a different calibration factor that is separately determined.

The following non-limiting example is introduced for illustrative purposes. It should be understood, however, that this disclosure is envisioned for use on instruments with one or multiple modules that require calibration such as a workcell. For example, the process described below can be applied separately for each module of a multiple-module instrument. Additionally, this disclosure is applicable for use on a single instrument as well as within multiple linked instruments.

In an example, a hematology instrument performs a quality control test on a known specimen. The instrument measures an amount of light reflected from the specimen and applies a calibration factor to create a recovered value. For example, if the instrument measures an output value, or a channel, of 156, and the instrument uses an initial calibration factor of one, then the instrument determines a recovered value of 156. The instrument can store one or more of the measured output value, the recovered value, or the calibration factor used for the particular quality control measurement.

The instrument can perform quality control runs on a periodic basis, for example, every day when a technician turns on the instrument, or on demand. During subsequent quality control tests, different measured output values are obtained by performing quality control tests. For example, four additional quality control tests performed at different times obtain output values of 157, 159, 160, and 162 respectively, with calibration gain factors of 0.989. 0.993, 0.893, and 0.919 respectively. In this example, the recovered values are 155.273, 157.887, 142.880, and 148.878 respectively.

Once a sufficient number of historical quality control tests have been executed, the instrument may perform a calibration based on the historical quality control tests. In an example, a sufficient number of quality control tests may be five, but any number is possible and the number can be adjusted as necessary.

Continuing with the example, the instrument accesses the recovered values, de-calibrates the recovered values, and calculates a representative value of the de-calibrated values. In this example, the instrument de-calibrates the recovered values of 156, then 155.273, 157.887, 142.880, and 148.878 to 156, 157, 159, 160, and 162, by dividing by their respective calibration gain factors. The instrument determines a representative value of the output values by calculating an average value, 158.8.

Continuing the example, the instrument accesses an expected value of 156. The instrument calculates a new calibration factor of 0.982.4 that when applied to the representative value, equals the expected value. The instrument updates the stored calibration factor in the data structure.

In an aspect, the instrument stores measured output values of a quality control instrument rather than a recovered value, i.e., calibrated value of the measurement. In this case, the instrument need not perform de-calibration and may calculate a representative value directly from the output values.

Subsequently, when testing a patient specimen, the instrument reads the calibration factor from the data structure and applies the factor to output values, thereby maintaining accurate results. The instrument stores the recovered value along with a timestamp indicating when the quality control test was performed to a data structure in internal non-volatile memory.

Disclosed solutions provide technical improvements in the field of laboratory instruments. More specifically, disclosed solutions improve the technological process of instrument calibration by improving instrument accuracy and reliability. Disclosed solutions minimize an effect to calibration of quality control results that are shifted due to environmental or other changes, bad quality control specimens, or user error. Additionally, disclosed systems reduced the need for manual calibration, as the time between failures that require intervention is reduced. For example, previous solutions required involving a remote technician, accessing device parameters from machine, and retesting a quality control specimen (including the manual loading or unloading of specimens). Further, by applying the disclosed solutions to multiple laboratory instruments, the reproducibility of results among instruments is improved, e.g., by ensuring that instruments are similarly calibrated.

Figure 1:
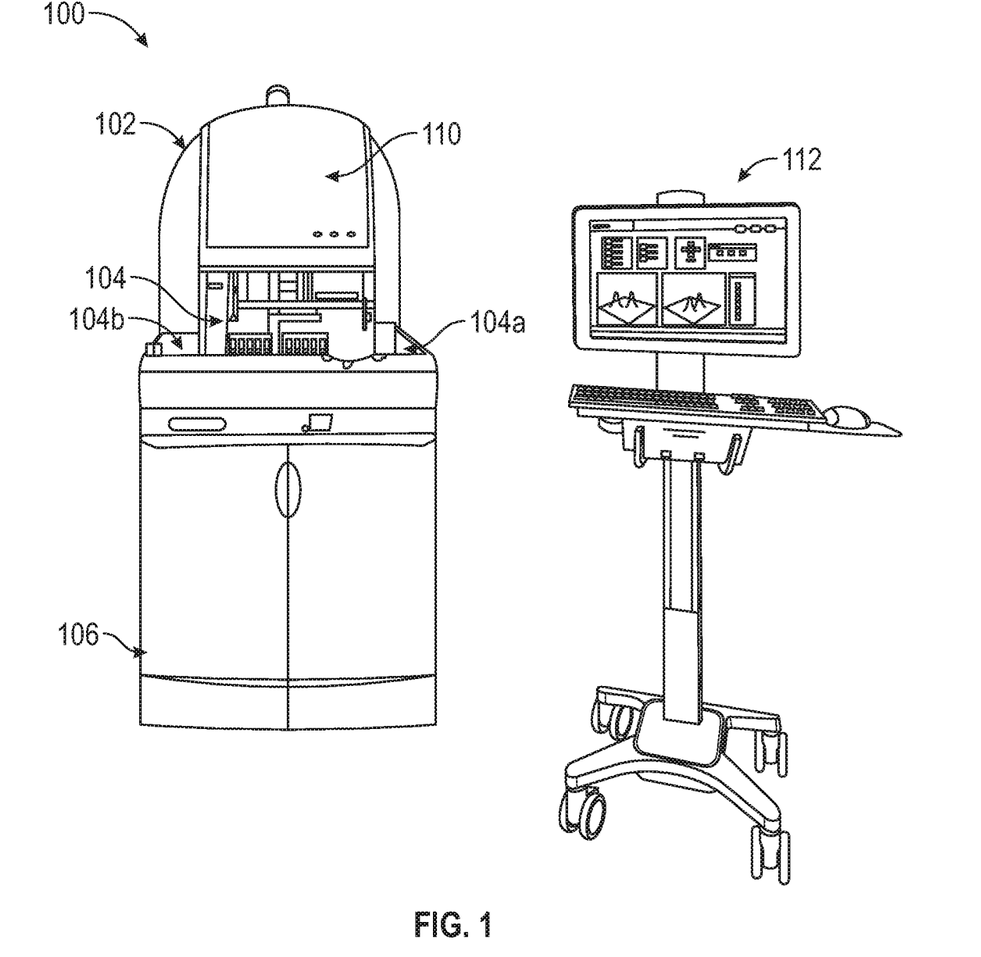
FIG. 1 depicts a front perspective view of a laboratory instrument, according to an aspect.

FIG. 1 depicts a front perspective view of a laboratory instrument 100. Instrument 100 receives patient specimens, performs tests such as blood analysis, urine analysis, body fluid analysis (e.g., cerebrospinal fluid, pleural fluid and/or synovial fluid) and the like, and provides the results to a laboratory technician, LIS, clinician, or other entity.

Instrument 100 includes a housing 102 with sides defining the front, back, left and right sides, top and bottom as illustrated. Instrument 100 can include a working deck 104 that incorporates readily accessible areas for an operator to add specimens for analysis and consumables for use in processing the specimens. Working deck 104 can include an input buffer 104a, where the specimens are provided, and an output buffer 104b, where the processed specimens are collected.

Instrument 100 can also include a transport shield 110 that restricts operator access to specimens when instrument 100 is operating. Instrument 100 can also include a storage location 106. Storage location 106 can include space for supplies such as quality control specimens, and can also provide technician access to the inner workings of instrument 100. Instrument 100 can include or receive consumables such as reagents for performance of a variety of functions, including, for example, sample preparation and instrument flushing or cleaning. Sufficient storage space for consumables can be provided on the system, permitting operation with minimal operator intervention for an extended time.

Instrument 100 also includes one or more computing systems 112 that can be used for operations such as data entry, analysis, quality control, or calibration. An example computing system is shown in more detail in FIG. 7. Computing system 112 can be programmed to store data such as measured output values, recovered values, calibration factors, etc., execute the quality control functions such as detecting when a quality control test has failed, identifying which instrument(s) in a workcell failed a quality control test, re-starting a quality control test, causing the instrument 100 to cease processing other specimens, redirecting patient specimens from an instrument in a workcell that has failed a quality control test to an instrument in a workcell that has passed a quality control test, and reporting the results, e.g., via the display, status light, or via an electronic message. Computing system 112 can also perform calibration functions as described herein. In one aspect, the computing system 112 can be external to instrument 100 (as shown) and connected via wireless or wired connection. In another aspect, the computing system 112 can be part of the instrument 100. Instrument 100 can include a light or a speaker to provide alerts to an operator. Alerts can indicate that a quality control test failed or that operator intervention is needed. For example, instrument 100 may include a light that changes to red in the event of a quality control issue that has stopped the instrument from operating, yellow for a warning, or green to indicate correct operation. An additional light, such as a blue or purple light, could be used to indicate that the instrument is ready to run but is not currently processing samples, for example, because the instrument has analyzed all of the samples in the input buffer 104a. Computing system 112 can connect to a remote device that can receive uploaded parameters from the instrument or receive commands such as initiating further quality control testing or diagnostics.

In one aspect, the computing system 112 can be external to instrument 100 (as shown) and connected via wireless or wired connection. In another aspect, the computing system 112 can be part of instrument 100. Instrument 100 can include a light or a speaker to provide alerts to an operator. Alerts can indicate that a quality control test failed or that operator intervention is needed. For example, instrument 100 may include a light that changes to red in the event of a quality control issue, yellow for a warning, or green to indicate correct operation. Computing system 112 can connect to a remote device that can receive uploaded parameters from the instrument or receive commands such as initiating further quality control testing or diagnostics.

Instrument 100 can be a single, enclosed system. For example, instrument 100 can receive specimens, perform tests, and output the specimens and results in isolation. Alternatively, instrument 100 can operate in conjunction with other instruments, for example in a workcell. Instrument 100 can detect a presence of a quality control specimen by scanning a bar code or other marking present on the specimen. In addition to or in lieu of a bar code or special marking, quality control specimens could be identified by cassettes or sample containers of a size, shape, color or other aspect distinguishable from patient samples. For example, quality control specimens could be presented in a tube that is taller than patient sample tubes, or has a tube cap of a different color, size or surface texture from a patient sample tube, such that the quality control specimens could be recognized by visual analysis. Instrument 100 may include markings to facilitate distinguishing different sample tubes, e.g., a mark that is visible above some kinds of sample containers but obscured by a portion of a different kind of sample container.

Figure 2:
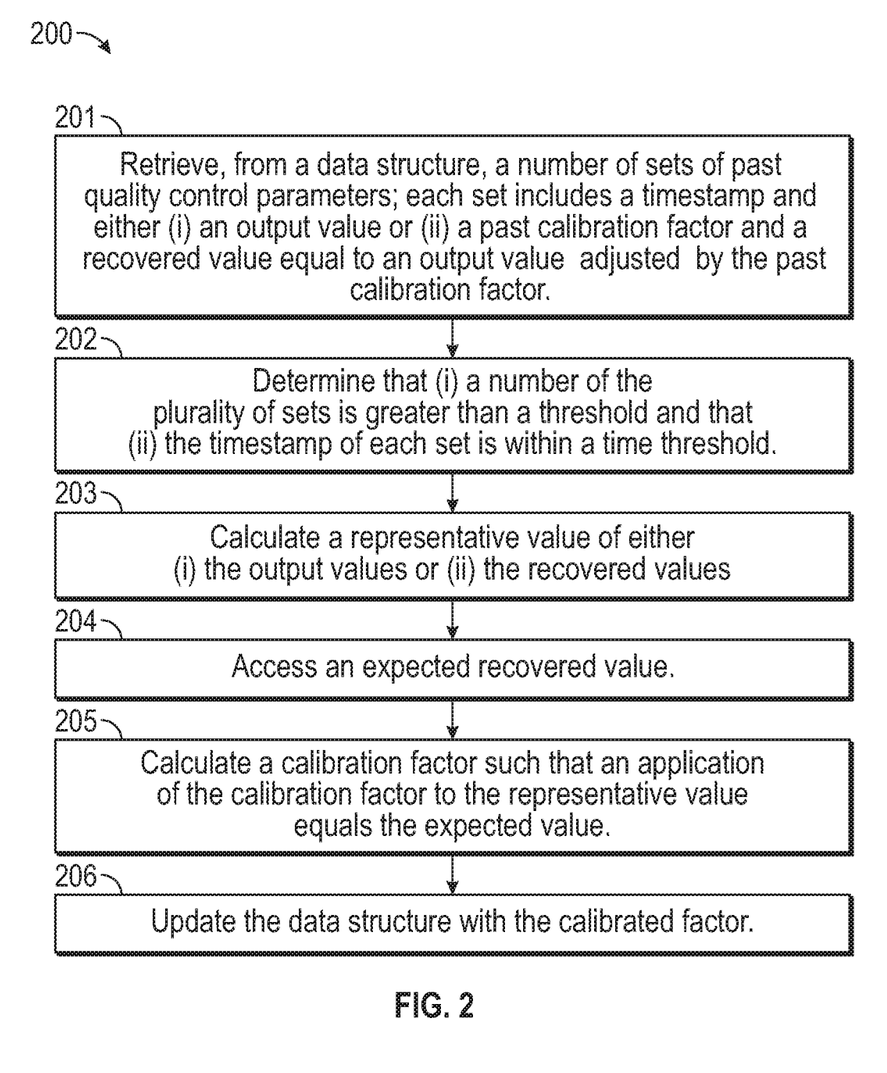
FIG. 2 depicts a flowchart illustrating an example of a process for performing automatic instrument calibration.

FIG. 2 depicts a flowchart illustrating an example of a process 200 for performing automatic instrument calibration. Process 200 can be implemented by instrument 100, a processing device therein, or another suitable instrument. Process 200 can be performed for each module of a multi-module instalment or for each parameter measured by a particular module. For example, an instrument may detect electrical conductance and a reflectance of light. Two or more instances of process 200 can execute in parallel to perform calibration of both multiple modules, e.g., conductance and reflectance. Alternatively, process 200 can operate in series.

In an aspect, automatic calibration can be enabled or disabled, for example using a button or switch on instrument 100, or using a setting entered via computing system 112.

At block 201, process 200 involves retrieving, from a data structure a number of sets of quality control parameters. The data structure can be retrieved from or stored in internal memory of computing system 112. Each set of past quality control parameters includes timestamp. Process 200 can operate by accessing either output values, i.e., measurement values from a laboratory instrument testing a quality control specimen, or recovered values, which are the output values adjusted by a calibration factor. The timestamp indicates when the recovered value was obtained or measured.

For example, each set of past quality control parameters also includes either (i) a measured output value or a past calibration factor and a recovered value equal to an output value adjusted by the past calibration factor, instrument 100 may displayed the recovered values to an end user or technician. Recovered values are de-calibrated, or adjusted, to remove the effect of calibration before such values are used in a calibration process such as process 200 that considers historical quality control values. A de-calibrated recovered value is close to or identical to the corresponding measured output value. Each known specimen has known, or expected, value for each specimen. Each module of an multi-module instrument has a separate expected value.

Figure 3:
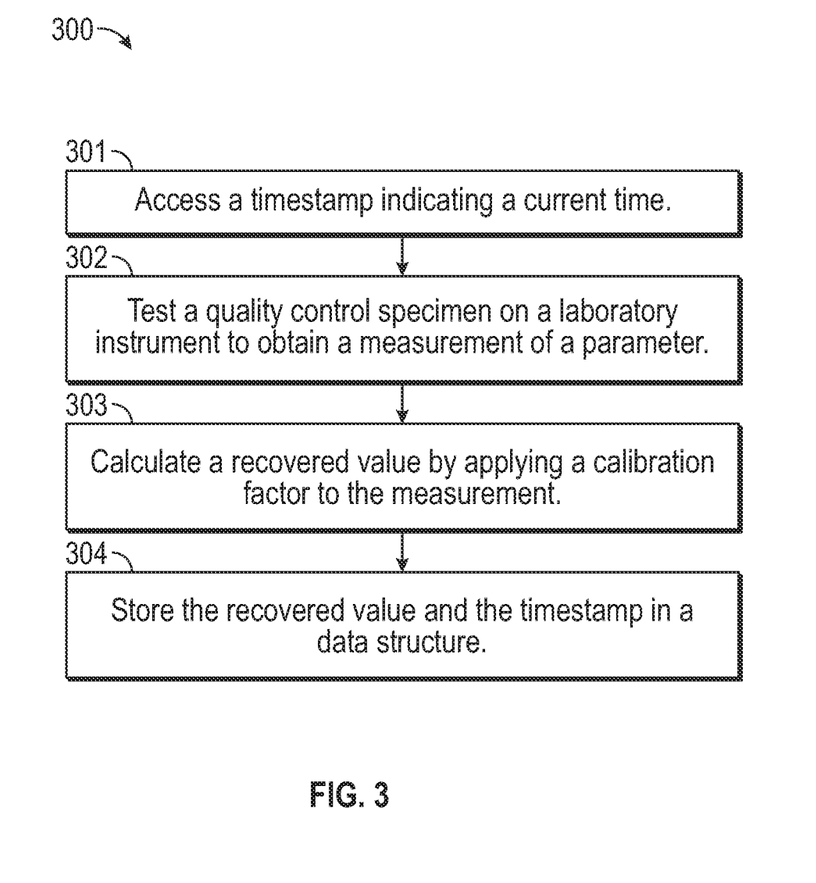
FIG. 3 depicts a flowchart illustrating an example of a process for performing qualm control.

FIG. 2 is discussed in conjunction with FIG. 3, which illustrates an example process for determining a quality control recovered value, but other processes can be used.

FIG. 3 depicts a flowchart illustrating an example of a process for performing quality control. Process 300 can be implemented by instrument 100, a processing device therein, or other suitable instrument. Instrument 100 can accumulate multiple quality control runs by executing multiple times and storing quality control values from different runs.

In an aspect, process 300 may involve determining that the quality control run is for system diagnostic purposes, and not for quality control testing. In this case, process 300 might not store the results obtained from the particular quality control test, or may clear all the previous quality control results in the data structure.

At block 301, process 300 involves accessing a timestamp including a current time. Instrument 100 can use the timestamps to ensure that the quality control parameters that are used for calibration are relevant. For example, quality control parameters obtained in winter with low humidity may not be relevant for calibration in summertime when the weather is more humid.

At block 302, process 300 involves testing a quality control specimen on a laboratory instrument to obtain a measurement of a parameter. The laboratory instrument may test the quality control specimen and obtain a measurement of the parameter such as luminance, reflectance, or conductivity. For example, instrument 100 may include a module that measures electrical conductivity of the known specimen. Instrument 100 obtains a output value of 156.

At block 303, process 300 involves calculating a recovered value by applying a calibration factor to the measurement. Instrument 100 may obtain a calibration factor from a data structure. The factor, calculated using a process such as process 200, may be used to adjust a output value to compensate for calibration. Alternatively, if process 200 has not yet executed, then the calibration factor may be a default value such as 1.0. Continuing the example, instrument 100 may apply the default factor of 1 to the output value, obtaining a recovered value of 156.

At block 304, process 300 involves storing the recovered value and the timestamp in a data structure. Instrument 100 stores recovered value of 156 in the data structure. Instrument 100 can later retrieve the recovered value and timestamp for use in a calibration, such as the calibration performed in process 200.

In an aspect, process 300 involves determining that the recovered value meets a set of criteria. Criteria can include passing quality control on a certain number of instrument modules, or outputting measurements that are within a certain tolerance. Instrument 100 can verify that a recovered value is within a tolerance or that an output value is within a tolerance. For example, if an output value is abnormal but within a tolerance, then instrument 100 can initiate a recalibration. Additionally, if the output value is outside the tolerance, then instrument 100 can detect that hardware recalibration or repair may be necessary and send an alert to a technician. In an aspect, if both the recovered value and the output values are outside their respective tolerances, then instrument 100 may continue fail and trigger an intervention by a technician.

Process 300 can repeat several times such that multiple runs of quality control data are available for calibration. Continuing the example, process 300 may execute four more times, obtaining recovered values of 157, 159, 160, and 162. The data structure therefore includes recovered values of 159, 157, 159, 160, and 162 and respective gain factors of 1, 0.989. 0.093, 0.893, and 0.919.

Returning to FIG. 2, process 200 continues calibration using the historical quality control values generated by a process such as process 300.

At block 202, process 200 involves determining that (i) a number of the plurality of sets is greater than a threshold and that the timestamp of each set is within a time threshold.

In an aspect, instrument 100 determines that a threshold number of sets of quality control parameters are available before proceeding with the calibration process. The last k historical de-calibrated recovered values (or output values) at time i can be represented by X=x(i−k), . . . x(i), where x(n) are individual de-calibrated recovered values (which are close to or exactly match the measured output values In an example, k is 5, but other numbers are possible. If less than the threshold number of sets are available, then calibration may not be performed. In this case, additional quality control tests can be performed, and upon reaching the threshold number of sets of quality control measurements, instrument 100 restarts process 200.

Additionally, or alternatively, instrument 100 can ensure that the sets of quality control measurements are sufficiently recent to warrant use in a calibration. If the sets are outside a time threshold, then instrument 100 can either discard the runs or not execute calibration. An example time threshold is fifteen days.

At block 203, process 200 involves calculating a representative value of either (i) the output values or the recovered values. The representative value can be represented by $\mu(i+1)=f(X)$, where $f(X)$ is a function. Example functions include mean, median, or mode of the recovered values. In the case of an instrument with multiple modules, different functions can be used for calculating a representative value of the recovered values.

If process 200 uses recovered values, then at block 203, instrument 100 performs an additional step of de-calibrating recovered values such that the effect of the calibration is removed. For example, for each recovered value, instrument 100 calculates a de-calibrated value $$x(i) = \frac{y(i)}{g(i)},$$

where y(i) is the recovered value for value i and g(i) is the gain for value i.

Continuing the example, instrument 100 obtains the recovered values of 156, 155.273, 157.887, 142.880, and 148.878 and the respective gain factors of 1, 0.989. 0.993, 0.893, and 0.919. Instrument 100 de-calibrates the recovered values by removing the gain factors, and obtains an average of the de-calibrated values of 156, 155.273, 157.887, 142.880, and 148.878, which is 158.8.

At block 204, process 200 involves accessing an expected recovered value instrument 100 accesses an expected recovered value from storage, via accessing a remote system, or by other means. For example, known specimens may be provided with a data sheet that can be scanned or keyed into computing system 112. Continuing the example, instrument 100 accesses an example expected recovered value of 156.

At block 205, process 200 involves calculating a calibration factor such that an application of the calibration factor to the representative value equals the expected value. Calibration factors can be multiplication, division, addition, or subtraction factors, or any other mathematical function. A calibration factor can be represented by $$g(i+1) = \frac{t}{\mu(i+1)},$$

where t is the expected value of the quality control parameter measurement given the known specimen. The calibration factor adjusts the output value to equal the recovered value. Continuing the example, instrument 100 would calculate a calibration factor of 0.9724.

In an aspect, instrument 100 calculates a calibration factor that adjusts the output value to be within a tolerance of the recovered value. Such an approach may be useful to account for data precision or rounding errors.

At block 206, process 200 involves updating the data structure with the calibration factor. The instrument then uses the calibration factor in future quality control tests. The calibration factor can be applied to the next specimen test.

For example, the application of a gain calibration factor can be represented by $y(i+1)=x(i+1)*g(i+1)$ where $y(n)$ is the recovered value at time n.

In an aspect, instrument 100 can determine that the calibration factor is greater than a threshold and take action. For example, if the calibration factor is outside a range of acceptable values, then the result may be unreliable. Therefore, instrument 100 can deactivate the instrument, send an alert to a technician, or mark measured specimens as unreliable. If the calibration factor is sufficiently far out-of-range, then calibration may not be possible, and instrument repair may be needed.

Figure 4:
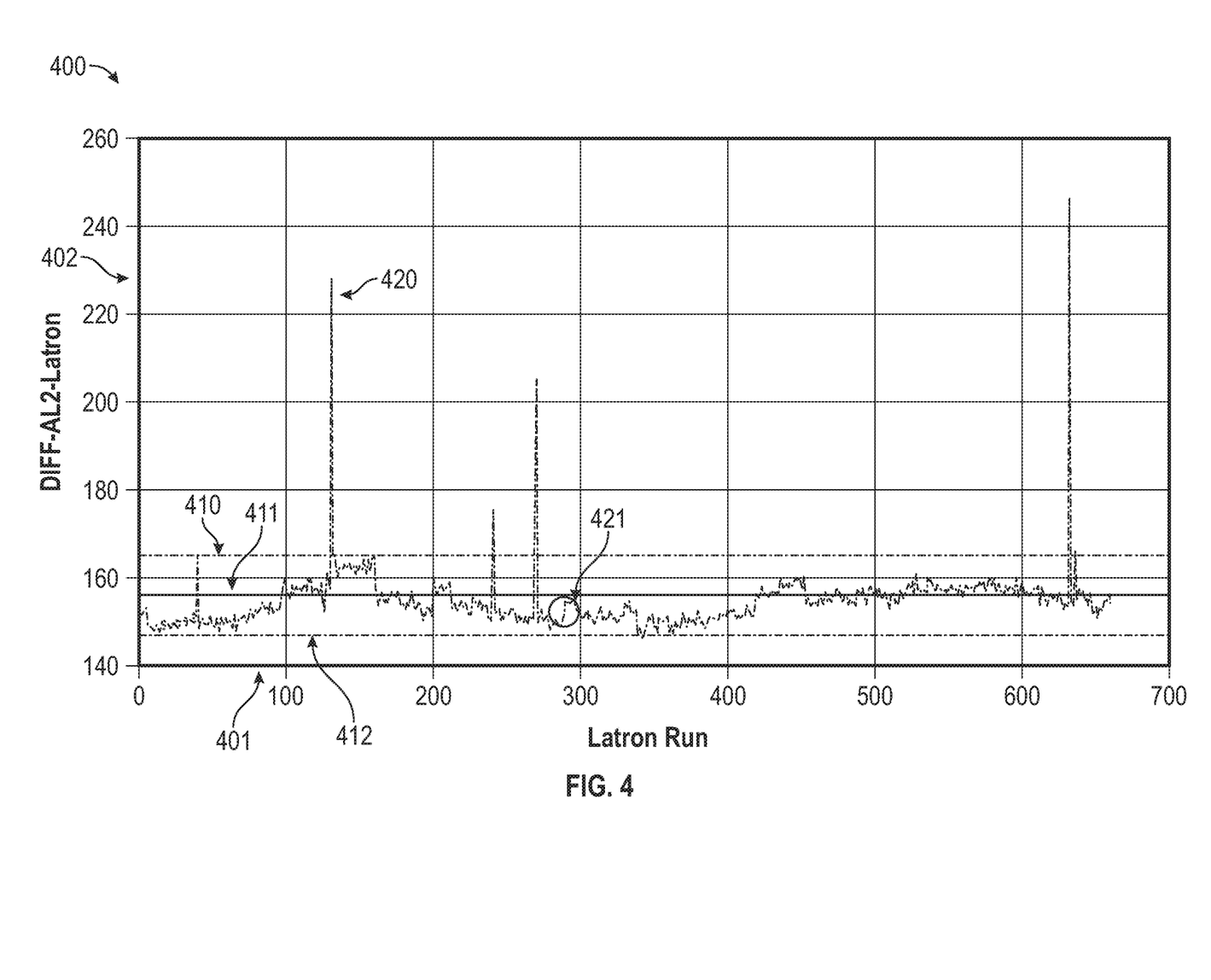
FIG. 4 depicts a graph illustrating recovered values obtained by quality control tests, according to an aspect.

FIG. 4 depicts a graph illustrating recovered values obtained by quality control tests, according to an aspect. FIG. 4 depicts graph 400. As shown, graph 400 includes horizontal axis 401, vertical axis 402, high threshold 410, expected value 411, low threshold 412, high value 420, and example transition 421.

Data depicted in graph 400 was gathered from instruments performing quality control tests using quality control specimens from the same batch. Therefore, each quality control specimen from the same batch can have identical expected values. Each value on horizontal axis 401 denotes a mode of a group of recovered values for each bead in a quality control specimen. A total of over 600 mode values are depicted, each mode value representing a particular quality control test. In an example usage scenario, the mode values are generated by one laboratory instrument over a period of approximately two years.

Vertical axis 402 denotes a parameter value. More particularly, the data depicted on graph 400 is a measurement of Axial light loss in an optical measurement. For example, the measurement can be obtained from a light source to light detector, and can be normalized based on a ratio of light before a bead is passed through an aperture of a sensor and after the bead is passed through an aperture of a sensor.

Expected value 411 indicates an expected value for the particular quality control specimen, high threshold 410 indicates an upper range of an expected recovered value, and low threshold 412 indicates a lower range of the expected recovered value. High value 420 denotes a quality control run that has an erroneous result. For example, high value 420 can be caused by an insufficient number of beads in the quality control specimen or a defective quality control specimen. Typically, the quality control test is subsequently re-run, and the erroneous result is confined to a single run. Transition 421 illustrates a case in which a calibration offset was adjusted to compensate for a low value. As can be seen, the data value shown in transition 421 increased sharply to be consistent with the low threshold 412.

Figure 5:
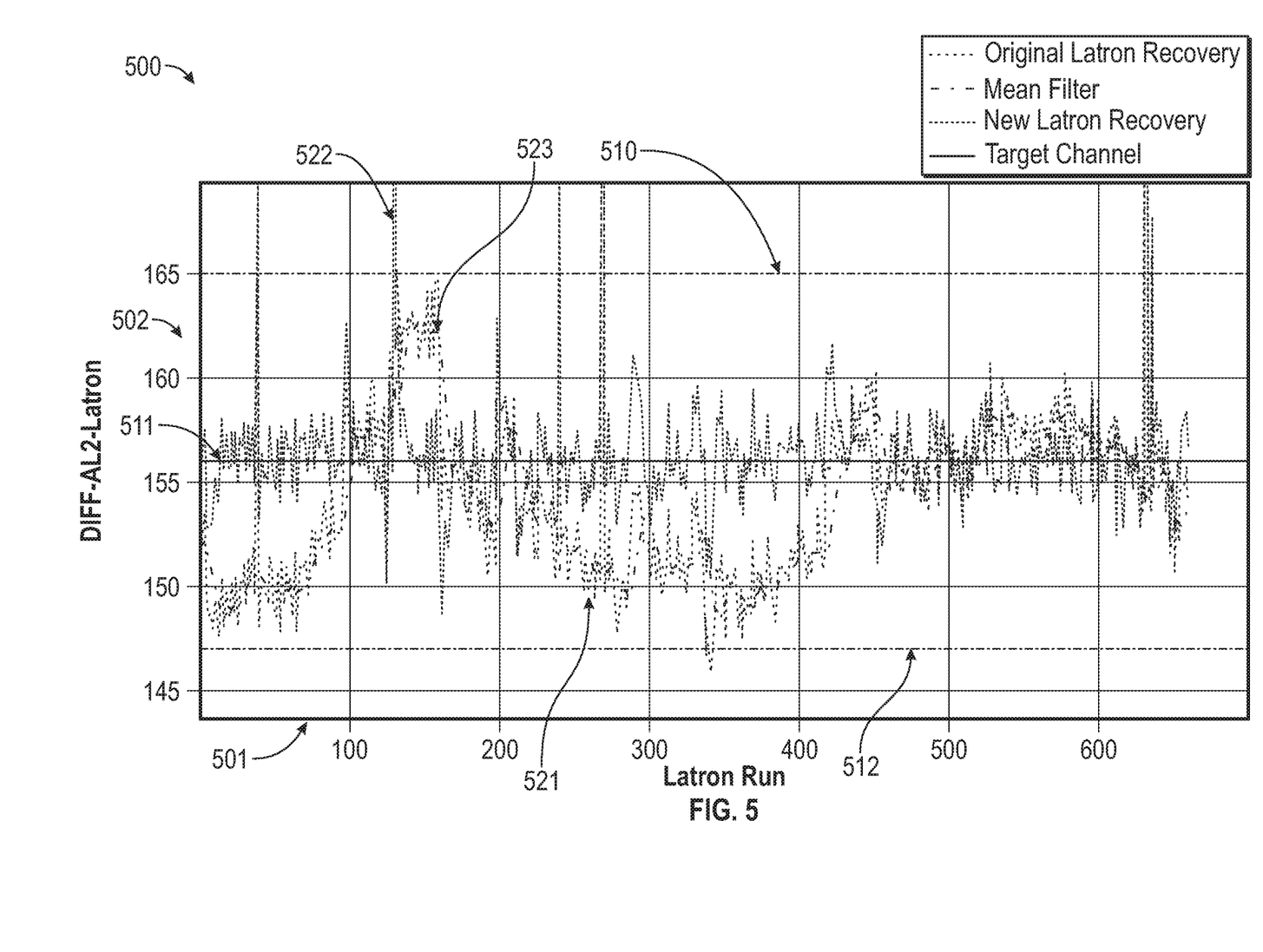
FIG. 5 depicts an example of results obtained via automatic calibration, according to an aspect.

FIG. 5 depicts an example of results obtained via automatic calibration, according to an aspect. FIG. 5 depicts graph 500. As shown, graph 500 includes horizontal axis 501, vertical axis 502, high threshold 510, expected value 511, low threshold 512, plot 521, plot 522, and plot 523.

Expected value 511 indicates an expected value for the particular quality control specimen, high threshold 510 indicates an upper range of the expected recovered value, and low threshold 512 indicates a lower range of the expected recovered value.

Plot 521 represents an unmodified recovered value. For example, each position on plot 521 represents a mode generated from aggregating each recovered values of each bead in a quality control specimen, as depicted in FIG. 4. In one example, a quality control specimen may include 5,000 beads. Plot 523 represents a mean of the last five quality control runs, as used by the disclosed system to perform calibration. Plot 522 represents simulated recovered values with calibration applied to correct the recovered value. As can be seen in plot 522, the some high peaks still exist but the recovered values are much closer to the expected value 511, illustrating the value of the disclosed system. The disclosed system is maintaining a low-frequency module while excluding high-frequency modules.

Disclosed systems provide improvements to instrument reliability. Table 1, below, depicts a performance assessment of an aspect of a solution disclosed herein. The data in Table 1 reflects the number of failures for a total of 2,113,069 quality control tests run on a pool of 3,864 instruments.

TABLE 1

| Failure Type | Mode | NRBC | Diff | Retic | Total |
| --- | --- | --- | --- | --- | --- |
| Type 1 | Auto calibration off | 53,774 | 34,280 | 25,368 | 91,405* |
|  | Auto calibration on | 15,728 | 12,596 | 7,599 | 30,454* |
| Type 2 | Auto calibration off | 32,384 | 27,560 | 15,050 | 58,487* |
|  | Auto calibration on | 20,449 | 22,098 | 11,312 | 42,584* |
| Type 3 | Auto calibration off | 32,838 | 29,093 | 18,005 | 68,724* |
|  | Auto calibration on | 32,578 | 28,789 | 17,815 | 68,188* |

The failures are divided into categories. The first column represents the type of failures. Type 1 is defined as when the mean or mode is outside the specification range but inside 1.2 times the specification range. Type 1 failures are likely caused by seasonality or failed calibration. The failures are close to the threshold but are nevertheless still failing. Type 2 failures are when the mean or mode is greater than 1.2 times the range but less than 2 times the range. Type 2 failures are likely not caused by seasonality. Type 3 failures are when the mean or mode is greater than three times the acceptable range and are likely caused by glitches.

The second column indicates the configuration mode. For each failure type, two rows are provided: "auto calibration off" and "auto calibration on." "Auto calibration off" indicates a previous calibration solution that does not use the disclosed system, i.e., does not take advantage of historical quality control data. "Auto calibration on" indicates the disclosed system. As can be seen, significant improvements are provided by the disclosed system in that the number of failures is sharply reduced in several cases.

The third, fourth, and fifth columns indicate failures on the Nucleated Red Blood Cell module (NRBC), White Blood Cell Differentiated module (Diff), and Reticulocyte module (Retic) modules in a hematology instrument. The sixth column indicates the total number of failures across different instrument modules. Note that failures can happen on multiple modules, therefore the separate failures for different modules are not mutually exclusive and overlap is possible.

Figure 6:
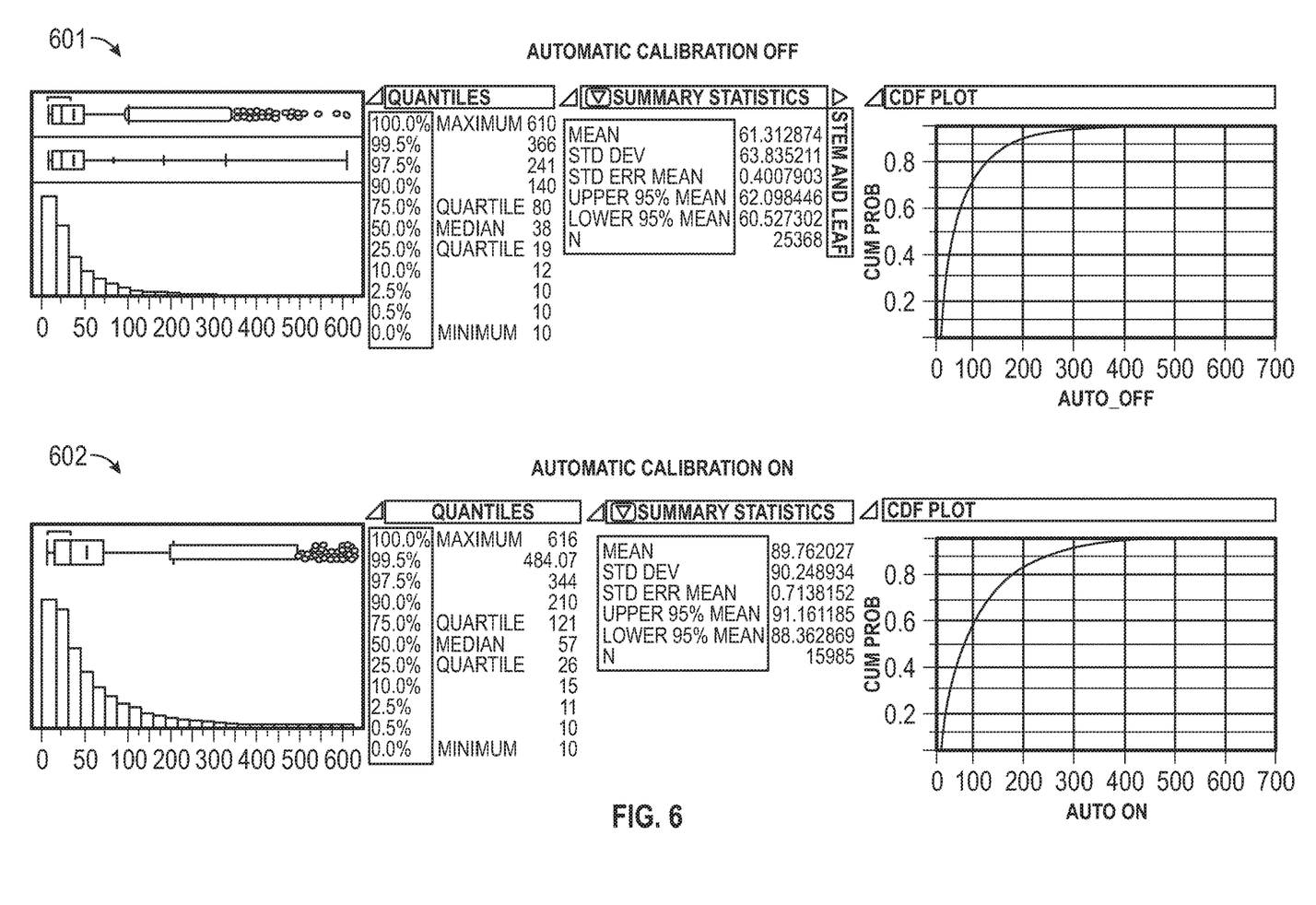
FIG. 6 depicts instrument failure statistics and graphs comparing automatic calibration on and automatic calibration off, according to an aspect.

FIG. 6 depicts instrument failure statistics and graphs comparing automatic calibration on and automatic calibration off, according to an aspect. FIG. 6 depicts plot 601 and plot 602. Plot 601 represents statistics of type 1 failures gathered when automatic calibration is turned off, i.e., using previous solutions. Plot 602 represents statistics of type 1 failures gathered when automatic calibration is turned on. Each of plot 601 and 602 include a probability distribution, quantiles, summary statistics such as mean, standard deviation, standard error mean, upper 95% mean, lower 95% mean, and a cumulative distribution function plot.

FIG. 6 illustrates an average increase from 60 to 90 days in between failures in seen when automatic calibration simulation is conducted. Data in FIG. 6 should be interpreted by taking into account that not all type 1 failures can be attributed to drifting or seasonality. As can be seen, the Cumulative Distribution Functions (CDFs) for the automatic calibration simulation illustrate that about 70% of Type 1 failures will occur within the 100 days from the previous failure as opposed to more than 82% when automatic calibration is not enabled.

Exemplary Computing Device

Figure 7:
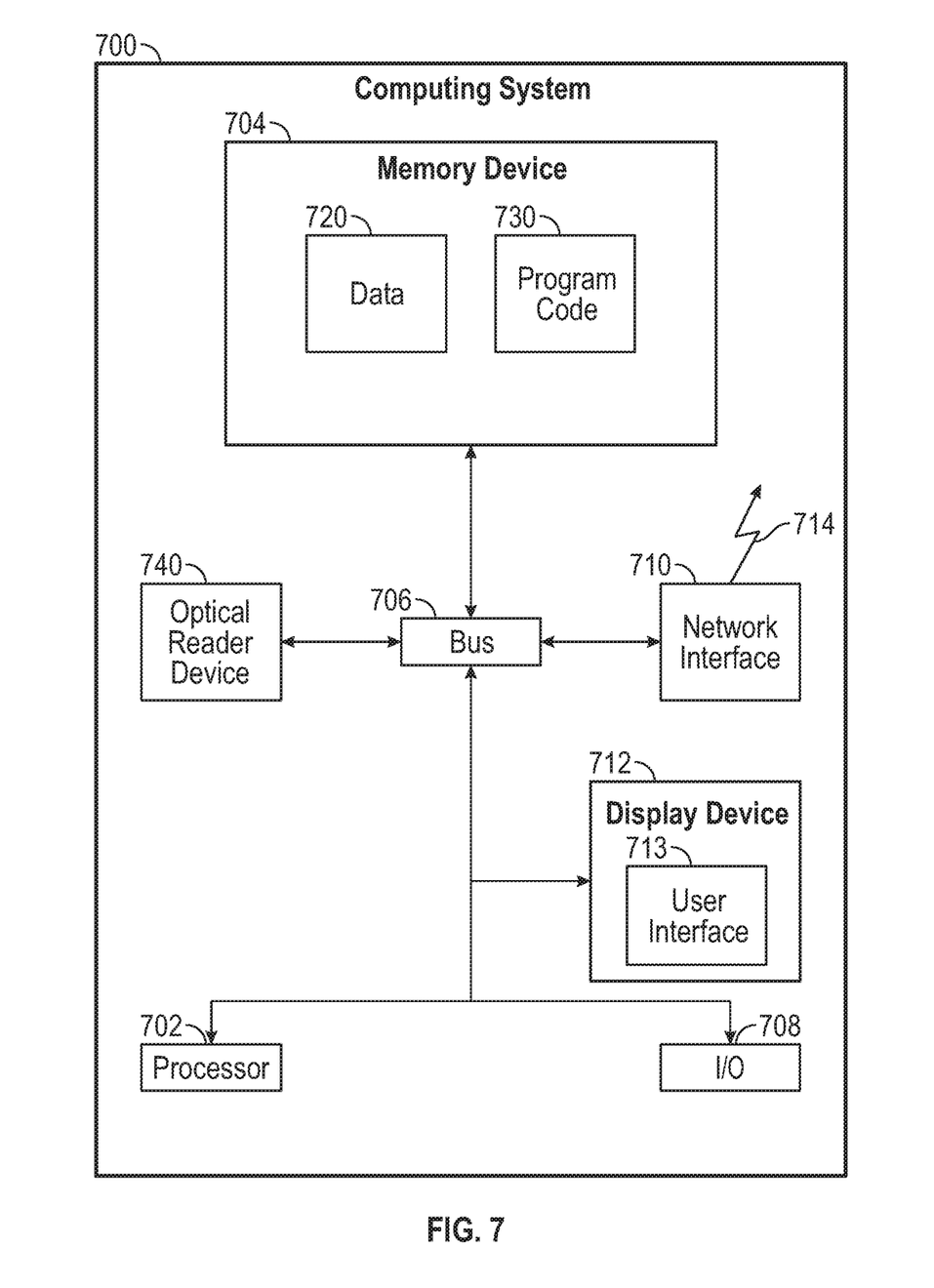
FIG. 7 depicts an exemplary computing system for instrument calibration, quality control, and operation.

FIG. 7 depicts an exemplary computing system for instrument calibration, quality control, and operation. Any suitable computing system may be used for performing the operations described herein. The depicted example of a computing device 700 includes a processor 702 communicatively coupled to one or more memory devices 704. The processor 702 executes computer-executable program code 730 stored in a memory device 704, accesses data 720 stored in the memory device 704, or both. Examples of the processor 702 include a microprocessor, an application-specific integrated circuit ("ASIC"), a field-programmable gate array ("FPGA"), or any other suitable processing device. The processor 702 can include any number of processing devices or cores, including a single processing device. The functionality of the computing device may be implemented in hardware, software, firmware, or a combination thereof.

The memory device 704 includes any suitable non-transitory computer-readable medium for storing data, program code, or both. A computer-readable medium can include any electronic, optical, magnetic, or other storage device capable of providing a processor with computer-readable instructions or other program code. Non-limiting examples of a computer-readable medium include a flash memory, a ROM, a RAM, an ASIC, or any other medium from which a processing device can read instructions. The instructions may include processor-specific instructions generated by a compiler or an interpreter from code written in any suitable computer-programming language, including, for example, C, C++, C#, Visual Basic, Java, or scripting language.

The computing device 700 may also include a number of external or internal devices, such as input or output devices. For example, the computing device 700 is shown with one or more input/output ("I/O") interfaces 708. An I/O interface 708 can receive input from input devices or provide output to output devices. One or more busses 706 are also included in the computing device 700. The bus 706 communicatively couples one or more modules of a respective one of the computing device 700.

The computing device 700 executes program code 730 that configures the processor 702 to perform one or more of the operations described herein. For example, the program code 730 causes the processor to perform the operations described in FIG. 2 or 3.

The computing device 700 also includes a network interface device 710. The network interface device 710 includes any device or group of devices suitable for establishing a wired or wireless data connection to one or more data networks. The network interface device 710 may be a wireless device and have an antenna 714. The computing device 700 can communicate with one or more other computing devices implementing the computing device or other functionality via a data network using the network interface device 710.

The computing device 700 can also include a display device 712. Display device 712 can be a LCD, LED, touch-screen or other device operable to display information about the computing device 700. For example, information could include an operational status of the computing device, network status, etc. Display device 712 can include user interface 713. User interface 713 can be any user interface such as a graphical user interface (GUI) that can display text, graphics, icons, visualizations, and the like.

The computing device 700 can also include optical reader device 740. Optical reader device 740 can be any optical recognition device such as a camera that can be configured to read and process a barcode or another visual marking on a specimen, label, or other printed material. Optical reader device 740 provides a scanned code to processor 702, which can process the code, for example, by accessing a table to determine any embedded parameters in the code such as name, identification number, specimen number, whether the specimen is a quality control specimen, etc.

In the preceding description, for the purposes of explanation, numerous details have been set forth in order to provide an understanding of various aspects of the present technology. It will be apparent to one skilled in the art, however, that certain aspects may be practiced without some of these details, or with additional details, or in varied combinations or sub-combinations of features of the aspects.

Having described several aspects, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific aspect may not always be present in variations of that aspect or may be added to other aspects.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the transducer" includes reference to one or more transducers and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. A laboratory instrument for testing patient specimens, the laboratory instrument comprising:
    a testing apparatus configured to perform testing on patient specimens and on quality control specimens; and
    a processor configured to retrieve, from a memory device, a plurality of sets of past quality control parameters, wherein each set comprises a timestamp comprising a time the set was collected, and wherein each set of the plurality of sets of past quality control parameters comprises either (i) an output value or
(ii) a past calibration factor and a recovered value equal to the output value adjusted by the past calibration factor;

wherein the processor is configured to
determine whether a number of the plurality of sets of past quality control parameters is greater than a threshold number of sets of past quality control parameters,
determine whether the timestamp of each set is within a time threshold, and
responsive to determining that the number of the plurality of sets is greater than the threshold number of sets and that the timestamp of each set is within the time threshold:
calculate a representative value of either the output values or the recovered values,
access an expected value of either the output values or the recovered values, and
calculate a calibration factor such that an application of the calibration factor to the representative value equals the expected value, and
update the memory device with the calibration factor.

2. The laboratory instrument of claim 1, wherein calculating the representative value comprises calculating one of a mean, a mode, or a median of the output value from each set of past quality control parameters.

3. The laboratory instrument of claim 1, wherein calculating the representative value further comprises:
de-calibrating each recovered value by removing the respective past calibration factor to provide de-calibrated recovered values, and
calculating one of a mean, a mode, or a median of the de-calibrated recovered values.

4. The laboratory instrument of claim 1, wherein updating the memory device causes the calibration factor to be used in future quality control tests.

5. The laboratory instrument of claim 1, wherein the processor is further configured to:
test a patient specimen on a laboratory instrument to obtain a measurement of a parameter;
calculate a recovered value by applying the calibration factor to the measurement; and
transmit the recovered value to a display device or in an electronic communication.

6. The laboratory instrument of claim 1, wherein the processor is further configured to:
access a timestamp indicating a current time;
test a quality control specimen on a laboratory instrument to obtain a measurement of a parameter;
calculate a recovered value by applying the calibration factor to the measurement; and
store the recovered value and the timestamp in the memory device.

7. The laboratory instrument of claim 1, wherein the processor is further configured to determine whether the recovered value is outside a recovered value threshold, and responsive to determining that the recovered value is outside the recovered value threshold, cease processing of further specimens and initiate the calibration of the laboratory instrument.

8. The laboratory instrument of claim 1, wherein the processor is further configured to determine whether a diagnostic run is occurring, and responsive to determining the diagnostic run is occurring, clear data in the memory device.

9. The laboratory instrument of claim 1, wherein the laboratory instrument comprises a hematology testing instrument, a flow cytometry instrument, a particle counter instrument, or a combination thereof.

10. A non-transitory computer readable storage medium having executable instructions stored thereon, that, when executed by a computing device, cause the computing device to perform operations comprising:
retrieving, from a memory device, a plurality of sets of past quality control parameters, wherein each set comprises a timestamp comprising a time the set was collected, and wherein each set of the plurality of sets of past quality control parameters comprises either
(i) an output value or
(ii) a past calibration factor and a recovered value equal to the output value adjusted by the past calibration factor;
determining whether a number of the plurality of sets of past quality control parameters is greater than a threshold number of sets of past quality control parameters and whether the timestamp of each set is within a time threshold; and
responsive to determining that the number of the plurality of sets is greater than the threshold number of sets and that the timestamp of each set is within the time threshold:
calculating a representative value of either the output values or the recovered values,
accessing an expected value of either the output values or the recovered values,
calculating a calibration factor such that an application of the calibration factor to the representative value equals the expected value, and
updating the memory device with the calibration factor.

11. The non-transitory computer readable storage medium of claim 10, wherein calculating the representative value comprises calculating one of a mean, a mode, or a median of the output value from each set of past quality control parameters.

12. The non-transitory computer readable storage medium of claim 10, wherein calculating the representative value further comprises operations comprising:
de-calibrating each recovered value by removing the respective past calibration factor to provide de-calibrated recovered values, and
calculating one of a mean, a mode, or a median of the de-calibrated recovered values.

13. A method for calibrating a module of a laboratory instrument, the method comprising:
retrieving, from a memory device, a plurality of sets of past quality control parameters, wherein each set comprises a timestamp comprising a time the set was collected, and wherein each set of the plurality of sets of past quality control parameters comprises either
(i) an output value or
(ii) a past calibration factor and a recovered value equal to the output value adjusted by the past calibration factor;
determining whether a number of the plurality of sets of past quality control parameters is greater than a threshold number of sets of past quality control parameters and whether the timestamp of each set is within a time threshold; and
responsive to determining that the number of the plurality of sets is greater than the threshold number of sets and that the timestamp of each set is within the time threshold:

calculating a representative value of either the output values or the recovered values, accessing an expected value of either the output values or the recovered values, calculating an updated calibration factor such that an application of the updated calibration factor to the representative value equals the expected value, and updating the memory device with the updated calibration factor; and performing a quality control test using the updated calibration factor.

14. The method of claim 13, wherein calculating the representative value comprises calculating one of a mean, a mode, or a median of the output value from each set of past quality control parameters.

15. The method of claim 13, wherein calculating the representative value further comprises:

de-calibrating each recovered value by removing the respective past calibration factor to provide de-calibrated recovered values, and calculating one of a mean, a mode, or a median of the de-calibrated recovered values.

16. The method of claim 13, further comprising determining whether the calibration is outside a predefined tolerance, and responsive to determining that the calibration factor is outside a predefined tolerance, ceasing performing calibration and sending an alert.

17. The method of claim 13, further comprising:

testing a patient specimen on a laboratory instrument to obtain a measurement of a parameter;

calculating a recovered value by applying the updated calibration factor to the measurement; and transmitting the recovered value to a display device or in an electronic communication.

18. The method of claim 13, further comprising:

accessing a timestamp indicating a current time;

testing a quality control specimen on a laboratory instrument to obtain a measurement of a parameter;

calculating a recovered value by applying the updated calibration factor to the measurement; and storing the recovered value and the timestamp in the memory device.

19. The method of claim 18, further comprising determining whether the recovered value is outside a recovered value threshold, and responsive to determining that the recovered value is outside the recovered value threshold, ceasing processing of further specimens and initiating the calibration of the laboratory instrument.

20. The method of claim 18, further comprising determining whether a diagnostic run is occurring, and responsive to determining a diagnostic run is occurring, clearing data in the memory device.

* * * * *